United States Patent
Engel

[11] Patent Number: 6,146,324
[45] Date of Patent: Nov. 14, 2000

[54] MAGNETIC ANALGESIC THERAPEUTIC DEVICE

[76] Inventor: Peter H. Engel, 619 S. June St., Los Angeles, Calif. 90005

[21] Appl. No.: 09/344,414

[22] Filed: Jun. 26, 1999

Related U.S. Application Data

[63] Continuation-in-part of application No. 09/030,184, Feb. 26, 1998, Pat. No. 5,993,375.
[51] Int. Cl.[7] .............................. A61N 1/00; A61B 17/52
[52] U.S. Cl. ................................................ 600/15; 600/9
[58] Field of Search .......................... 600/9, 15; 128/872, 128/869, 873, 876; 602/41, 78

[56] References Cited

U.S. PATENT DOCUMENTS

| | | | |
|---|---|---|---|
| 4,549,532 | 10/1985 | Baermann | 600/9 |
| 5,450,858 | 9/1995 | Zablotsky et al. | 128/876 |
| 5,746,213 | 5/1998 | Marks | 128/686 |
| 5,882,292 | 3/1999 | Miyaguchi | 600/9 |

*Primary Examiner*—Cary O'Connor
*Assistant Examiner*—Navin Natnithithadha
*Attorney, Agent, or Firm*—Fattibene & Fattibene; Arthur T. Fattibene; Paul A. Fattibene

[57] ABSTRACT

A therapeutic magnetic and analgesic pad or bandage formed of opposed strips interconnected to define a space or pocket therebetween for receiving a plurality of permanent magnets for generating a magnetic field to effect healing and/or reducing pain of an injured body part. The strip of the bandage or pad adapted to be placed in contact with the injured body part is formed of a synthetic water insoluble resin material which is impregnated with an analgesic ingredient in a manner whereby the analgesic ingredient is gradually released in a dry volatile state and imparted to the injured body part to synergistically further minimize pain and enhance healing.

23 Claims, 5 Drawing Sheets

MAGNETIC ANALGESIC THERAPEUTIC DEVICE

RELATED APPLICATION

This application is a continuation in part application of my prior U.S. Pat. No. 5,993,375, for Modular Magnetic Therapy Device, Ser. No. 09/030,184 filed Feb. 25, 1998.

FIELD OF THE INVENTION

The present invention relates in general to a magnetic therapy device and more particularly to a magnetic analgesic bandage or pad to promote healing and reduce or alleviate pain.

BACKGROUND OF THE INVENTION

The use of magnetic fields to promote healing and reduce pain is well known in the medical profession. There have been many studies in which it has been found that the use of a magnetic field can speed up post-operative healing. Additionally, there have been many studies in which the use of a magnetic field helps to alleviate pain due to muscle strains, tennis elbows, sore muscles, lower back pain, arthritis and the like. While there have been many different theories advanced as to why magnetic therapy works, it is still not clearly understood exactly how magnetic therapy aids in healing and in reducing pain. However, it is clear that many people's lives have been greatly improved by the use of magnetic therapy. Many devices have, therefore, been developed to practice magnetic therapy. One such magnet device for therapeutic use is disclosed in U.S. Pat. No. 4,549,532 entitled "Flexible Magnetic Sheet for Therapeutic Use" issuing to Baermann on Oct. 29, 1985, which is herein incorporated by reference. Therein disclosed is a permanent magnet sheet having alternating poles for applying a magnetic field to portions of the body for therapeutic purposes. Magnetic therapy devices generally take the form of placing a specially adapted permanent magnet pad adjacent a particular portion of the body. Accordingly, there are separate specialized products specifically adapted for back pain, neck pain, elbow pain, wrist pain, knee pain, and other various parts of the body. Often, an individual wishing to benefit from magnetic therapy is required to purchase a relatively large number of specialized devices for placing a permanent magnet adjacent different portions of the body. This is often inconvenient and expensive. Accordingly, there is a need for an improved permanent magnet device for use in magnetic therapy that can be applied easily to different locations of the body.

Relief of pain, particularly that resulting from a sport's injury and/or from sprained or strained muscles, was also heretofore achieved by the application of topical medical ointments or fluids such as liniment, oil of wintergreen, and other topical preparations that include a suitable analgesic ingredient. Such topical preparations, while effective, are messy and likely to soil any clothing with which they may come into contact.

BRIEF SUMMARY OF THE INVENTION

An object of this invention is to provide a therapeutic device capable of achieving the benefits afforded by both magnetic therapy and the topical application of medical preparations such as liniment, oil of wintergreen, and the like which imparts an analgesic effect on the affected body part.

Another object is to provide an improved therapeutic magnetic pad or bandage for the relief of pain by the application of magnetic therapy to the injured body portion supplemented by the application of an analgesic ingredient to further enhance the alleviation of pain.

Another object of this invention is to provide a therapeutic device for imparting both magnetic and analgesic therapy to an injured body part without the mess and soiling resulting from the heretofore direct application of topical ointments and analgesic fluids to the injured body part.

Another object of this invention is to provide an improved magnetic therapy device which is simple in construction and use, and which is relatively inexpensive to manufacture.

Another object of this invention is to provide a therapeutic magnetic device containing an analgesic ingredient which is gradually released to the adjacent body part over a period of time.

Another object of this invention is to provide a magnetic therapeutic device for relieving pain containing an analgesic ingredient to further reduce the discomfort of muscular aches and pains.

It is an object of the present invention to eliminate the need for a variety of special purpose magnetic therapy devices.

It is another object of the present invention to make magnetic therapy more cost effective and convenient.

It is an advantage of the present invention that the modular pads may be configured in any shape.

It is another advantage of the present invention that the magnetic field pattern and intensity can be varied.

It is a feature of the present invention that a perimeter of one surface has a fastener material and an opposing surface has a mating fastener material.

It is another feature of the present invention that one surface is padded and the opposing surface has a mesh covering.

The foregoing objects and other features and advantages are attained by a therapeutic bandage or pad in the form of a modular pad as described in my co-pending application Ser. No. 09/030,184 filed Feb. 25, 1998 for a Modular Magnetic Therapy Device which is incorporated herein by reference, or as an elongated bandage arranged to be wrapped about the injured body part. In either form, the bandage or pad is formed by opposed planar surfaces formed of sheet material having secured therebetween a plurality of small therapeutic permanent magnets arranged to generate a strong magnetic field. In accordance with this invention, one of said sheets, which is adapted to be placed in contact with the injured or sore portion of the body is formed of a preformed synthetic water insoluble resin that is subsequently impregnated with a medicinal agent or ingredient, e.g. methyl salicylate or other analgesic ingredient having an essential oil base. The arrangement is such that the impregnated sheet containing the analgesic ingredient is essentially dry to the touch. Yet, due to the nature of the selected resin and the manner in which it is impregnated with the medicinal or analgesic ingredient, the medical or analgesic material is gradually released to the adjacent injured body portion whereby the analgesic ingredient in cooperation with the magnets enhances the healing process.

DETAILED DESCRIPTION OF THE PREFERRED EMBODIMENTS

Figure 1:
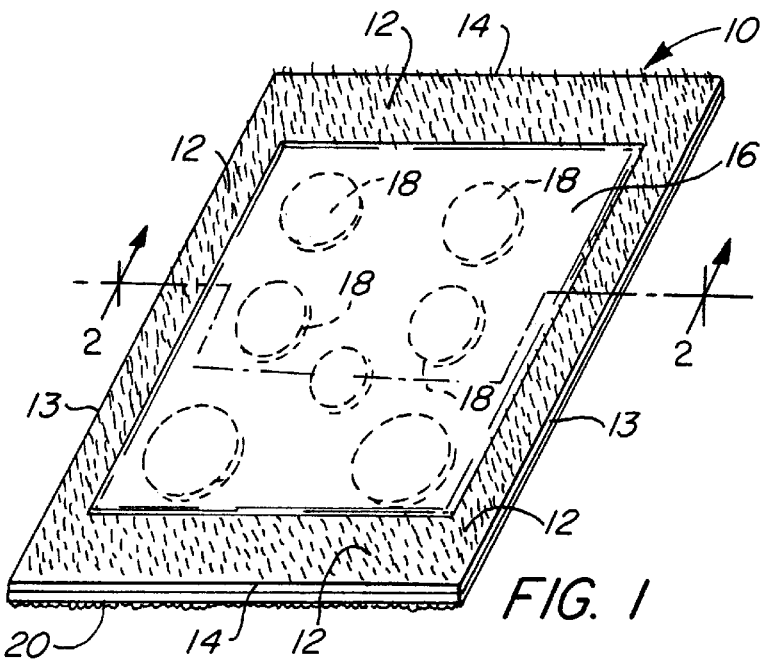
FIG. 1 is a perspective view of a single pad of the present invention.
Figure 1A:
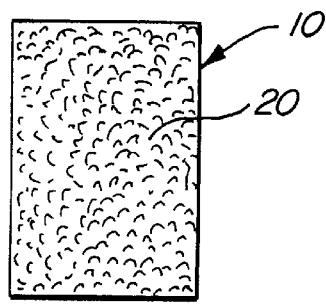
FIG. 1a is a plan view of a single pad of the present invention.

FIG. 1 illustrates a pad 10 having a first and second substantially planar surface forming therebetween a pocket or space. A first planar surface has longitudinal edges 13 with a fastener material 12 thereon, such as a hook-type fastener material. The first planar surface also has lateral edges 14 with a fastener material 12 thereon, which may also be a hook-type fastener material. Accordingly, the first planar surface of pad 10 has a perimeter of a first fastener material, such as a hook-type fastener material. Bounded by the longitudinal edges 13 and the lateral edges 14 is a bounded portion 16. The bounded portion 16 is covered with a mesh or woven fabric. Placed within the pocket or space defined by this bounded portion 16 and covered by the mesh or woven fabric are a plurality of permanent magnets 18. The permanent magnets 18 may take a variety of shapes such s square or rectangular, but are illustrated as being circular. The permanent magnets may be made of any conventional permanent magnet material such as Ceramic 5, having a Gauss rating of 3950. However, magnets 18 may also be made of a variety of known rare earth materials used to make a permanent magnet and having a relatively strong magnetic field. The Gauss rating of the magnets may vary from as low as 1200 to 11,000 m depending upon the desired application. On the opposing planar surface of pad 10 is a mating fastener material 20, such as a pile or loop-type fastener material. The hook-type and mating loop-type fastener materials are generally known and sold under the trademark VELCRO fastener. While hook-type and mating loop-type fastener materials are preferred, any other fastener and mating fastener materials may be used. FIG. 1a is a plan view of a single modular pad 10 illustrating the opposing substantially planar surface having the entire surface covered with the pile or loop-type mating fastener material 20.

Figure 2A:
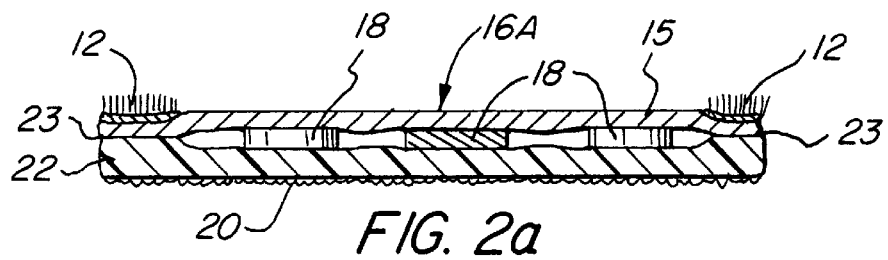
FIG. 2a is a cross section view similar to FIG. 2 illustrating a modified form of the invention.
Figure 2:
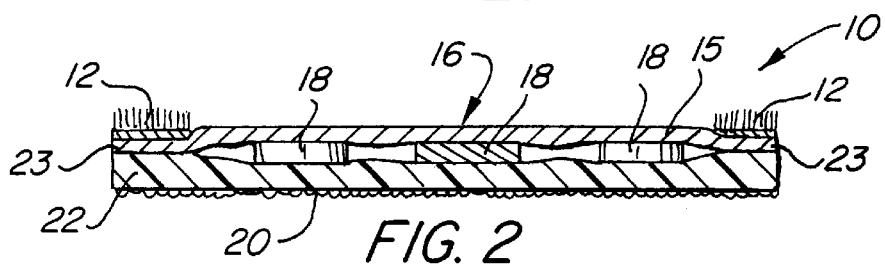
FIG. 2 is a cross section taken along line 2—2 in FIG. 1.

FIG. 2 is a cross section taken along line 2—2 in FIG. 1 and better illustrates the construction of the paid 10. A foam pad 22, such as neoprene, has a pile or loop material 20 attached thereto. The foam pad 22 forms a substantially planar surface. The mating fastener pile or loop material 20 preferably covers the entire planar surface of the one side of the foam pad 22. This permits a mating hook-type fastener material 12 to be attached anywhere on the surface. Additionally, the foam pad 22 is sufficiently flexible to adapt to different portions of the body. Attached to the opposing side or planar surface of foam pad 22 is a mesh or woven fabric 15 forming a bounded portion 16. Attached to the mesh fabric 15 along both the longitudinal edges and lateral edges is fastener material 12. The fastener material 12 may be adhered to the mesh fabric 15 by any conventional means, such as stitching 23. Accordingly, a pocket or space is formed between the mesh or woven fabric 15 and the foam material 22 within which is placed a plurality of permanent magnets 18. The foam pad 22 is attached to the mesh or woven fabric 16 by adhesive or any other conventional means, such as stitching 23.

Figure 3:
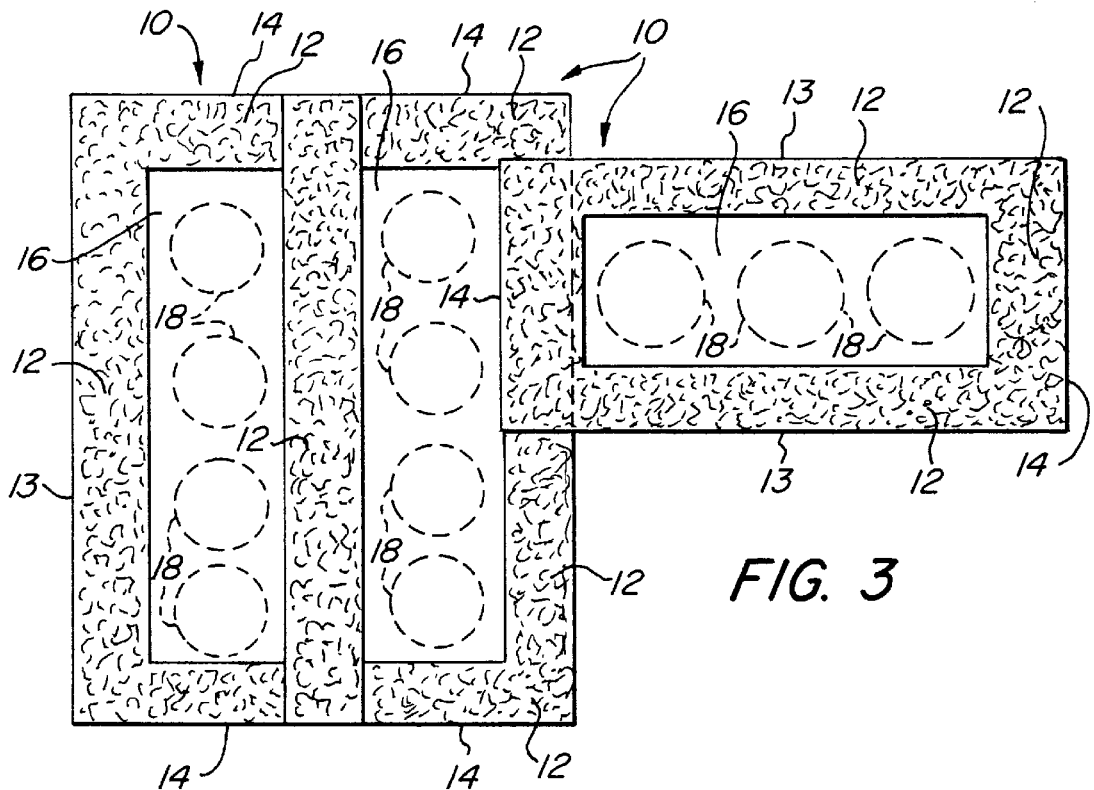
FIG. 3 is a plan view illustrating a plurality of pads embodying the invention attached together.

FIG. 3 is a plan view illustrating a plurality of pads 10 attached or fastened together. Two pads 10 are attached by longitudinal edges 13 and another pad 10 is attached by a lateral edge 14 to the longitudinal edge 13 of another pad. A fastener material 12 along the perimeter edges of the pads 10 is used to attach to the opposing surface of another pad having a mating pile or loop-type fastener material 20, as illustrated in FIG. 1 and FIG. 2. Preferably, the one fastener material is a hook-type fastener material and the other mating fastener material is a loop-type fastener material. Such a hook-type and loop-type fastener material are commonly referred to as, and available under, the trademark VELCRO fasteners. Clearly, the fastener materials could be reversed such that the loop or pile fastener material is placed around the peripheral edge of the pads 10 and the mating hook-type fastener material is placed on the opposing planar surface of the pads 10. Accordingly, the structure of the pads 10 of the present invention permit the pads 10 to be fastened together in a modular manner forming any desired shape. This permits the creation of a magnetic therapy device having any desired shape or magnetic field for placement adjacent any part of the body. Additionally, the pads 10 may be stacked one on top of another to vary the magnetic field intensity applied to a part of the body.

Figure 4:
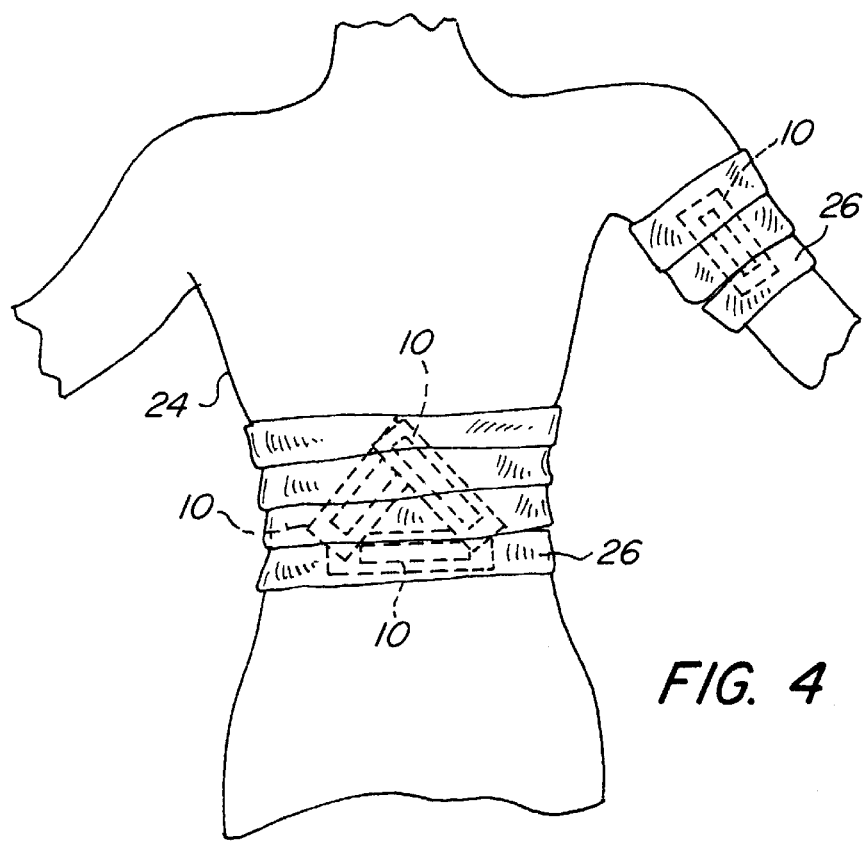
FIG. 4 is a schematic illustration of the application of the present invention to a body.

FIG. 4 schematically illustrates the placement of a plurality of modular pads 10 on the body of a person. Three pads 10 are illustrated configured in a triangular shape and placed on the torso of a body 24. A wrap 26 is used, such as an elastic bandage or other suitable or equivalent material, to hold the pads 10 in position adjacent the area of the body to be treated. Additionally illustrated is the placement of a single pad 10 on a portion of an arm of the body 24. This pad 10 is similarly held in position with an elastic bandage or a wrap 26. Accordingly, it should be appreciated that a plurality of pads 10 containing permanent magnets can be configured in any desired shape and positioned adjacent any portion of the body 24. Magnetic therapy can therefore be provided to any portion of the body without the need for many different specialized devices. Additionally, the modular pads 10 may be positioned in any desirable configuration to provide a predetermined magnetic field location and intensity, depending upon the therapy desired or needs of the individual.

Figure 5:
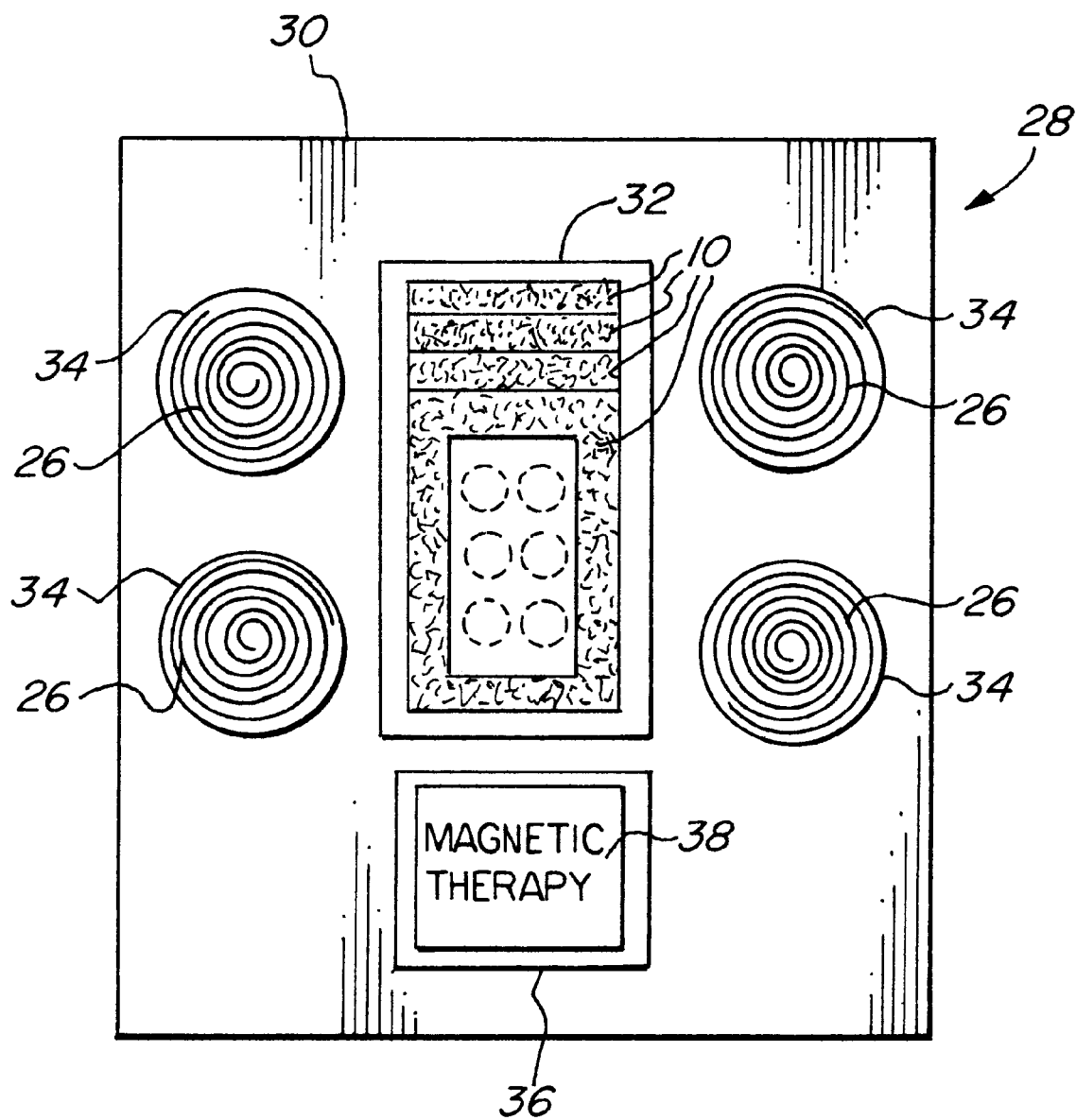
FIG. 5 is a plan view of a magnetic therapy kit.

FIG. 5 is a plan view of a magnetic therapy kit 28. A plastic tray 30 has a pad well 32 therein for holding a plurality of pads 10. A plurality of wrap wells 34 are formed in the plastic tray 30, each for holding a coiled elastic wrap 26. A book well 36 may also be formed in the plastic trays 30 for holding a magnetic therapy book 38. The kit 28 provides a convenient package providing the required items for applying magnetic therapy to any part of the body.

The present invention greatly facilitates the practice of magnetic therapy. The present invention provides great flexibility in the application to different parts of the body a magnetic field to reduce or alleviate pain or to promote healing. The structure of the present invention permits the modular pads to be very easily attached together, forming any desired shape and magnetic field. This provides great flexibility in applying a magnetic field, as well as making magnetic therapy more economical, because many different specialized pads for different parts of the body do not have to be individually purchased. Additionally, the present invention provides for the placement of a permanent magnet adjacent portions of the body for which there are currently no available specialized pads.

The pad 10 as herein described may also be formed so as to liberate an analgesic material to the adjacent injured body portion to hasten the healing and/or to further minimize or relieve the pain or soreness of the injured body part. This is attained by forming the facing or covering sheet 16 of pad 10 out of a synthetic water insoluble preformed resin 16A, as shown in FIG. 2a, which may be either plasticized or unplasticized. Suitable resin material for forming the facing sheet 16A of pad 10 may be selected from the group consisting of polyvinyl chloride, polyvinyl acetate, polyvinyl formal, polyvinyl acetal, polystyrene and polyurethane, formed as a film or sheet having imperforate portions wherein the imperforate portions of the plastic or resin sheet material 16A is impregnated with a medicinal or analgesic material having an essential oil base such as camphor, oil of wintergreen, methyl salicylate or eucalyptus.

The impregnation of the essential oil based medicament or analgesic material is achieved by emulsifying the medicinal or analgesic material with a suitable surfactant in water in accordance to the method described in U.S. Pat. No. 3,688,985 granted Sep. 5, 1972. A synthetic resin sheet 16A, treated with the emulsion so formed, causes the finally emulsified volatile matter of the medicinal or analgesic material to enter the imperforate portions of the synthetic resin sheet 16A. In doing so, a very small quantity of water is carried along with the volatile matter entering the resin sheet 16A. The resin material or sheet 16A is then dried of any excess fluid so that it feels dry to the touch. When dried, the resin sheet 16A is impregnated with the volatile matter so that the volatile analgesic material is gradually released over a period of time. When pad 10 is constructed with a face sheet 16A formed of a synthetic resin material and impregnated as herein described, the arrangement is such that analgesic material is gradually released to impart a further beneficial effect to the injured body part, which, together with the action of the magnetic field imparted by the magnets, will tend to further minimize pain and hasten healing by enhancing the blood circulation through the injured body part. In all other respects, the pad 10 of FIG. 2a is constructed as hereinbefore described with respect to FIGS. 1 to 4.

Figure 6:
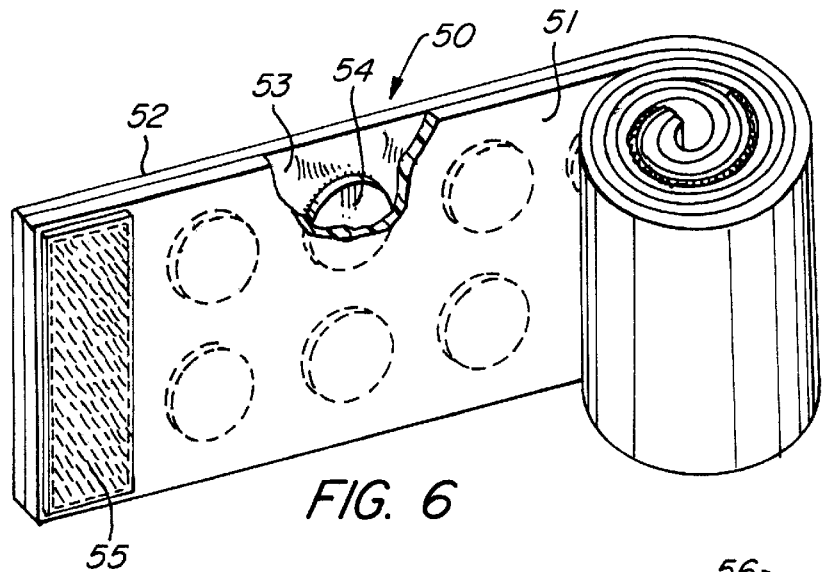
FIG. 6 is a perspective view of a modified bandage construction embodying the invention.
Figure 7:
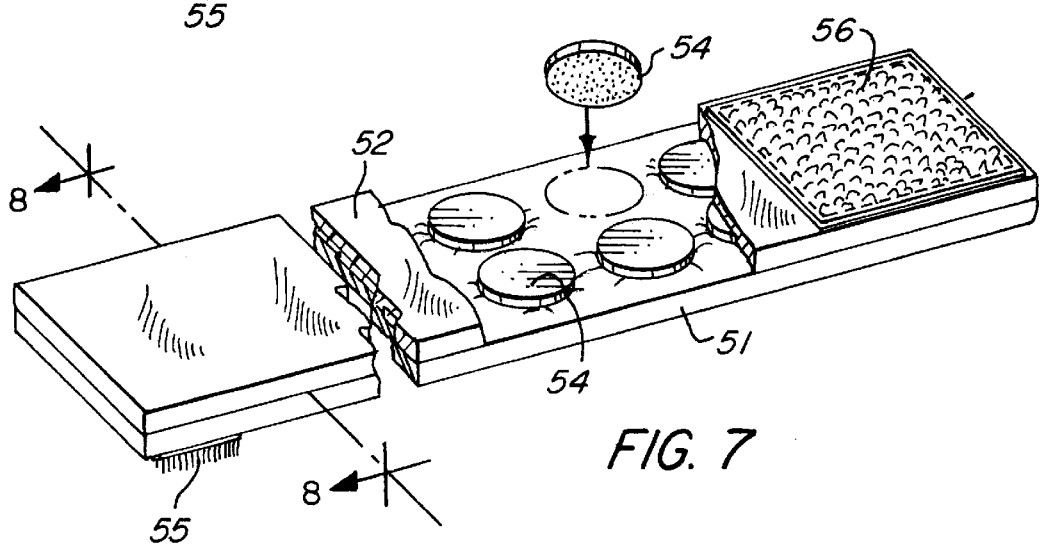
FIG. 7 is a perspective view of the bandage of FIG. 6 in the unrolled position.
Figure 8:
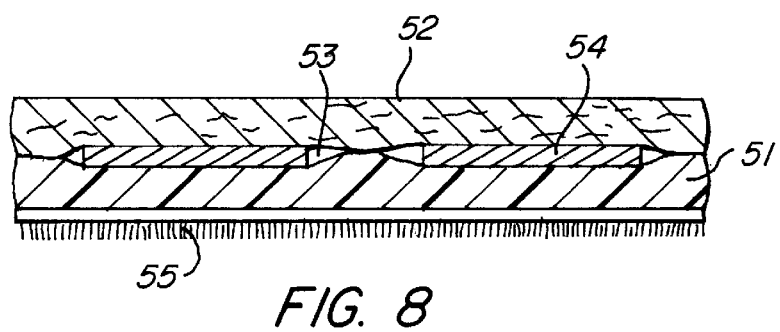
FIG. 8 is a sectional view taken along line 8—8 on FIG. 7.

FIGS. 6 to 8 illustrate a further embodiment illustrated in the form of a bandage or wrap 50 which can be readily coiled to form a roll type bandage. As shown, the bandage or wrap 50 comprises an elongated plastic facing sheet 51 which is impregnated with a suitable medicinal or analgesic material having an essential oil base as hereinbefore described, e.g. methyl salicylate, oil of wintergreen or camphor and the like. Secured to the facing sheet 51 is a cover sheet 52 which may be formed of a suitable fabric material such as cotton, linen or other suitable bandage type material. It will be understood that the facing sheet 51 and cover sheet 52 are suitably secured together by fastening means about their respective periphery as e.g. by stitching or adhesive so as to define therebetween a space or pocket 53. Interposed in the space 53 between facing sheet 51 and cover sheet 52 are a plurality of permanent magnets 54 that are spaced both laterally and longitudinally along the entire length of bandage 50. The respective magnets 54 are maintained in their relative spaced relationship between sheets 51 and 52 by any suitable means, e.g. by adhesive, stitching or other means.

Figures 9, 10:
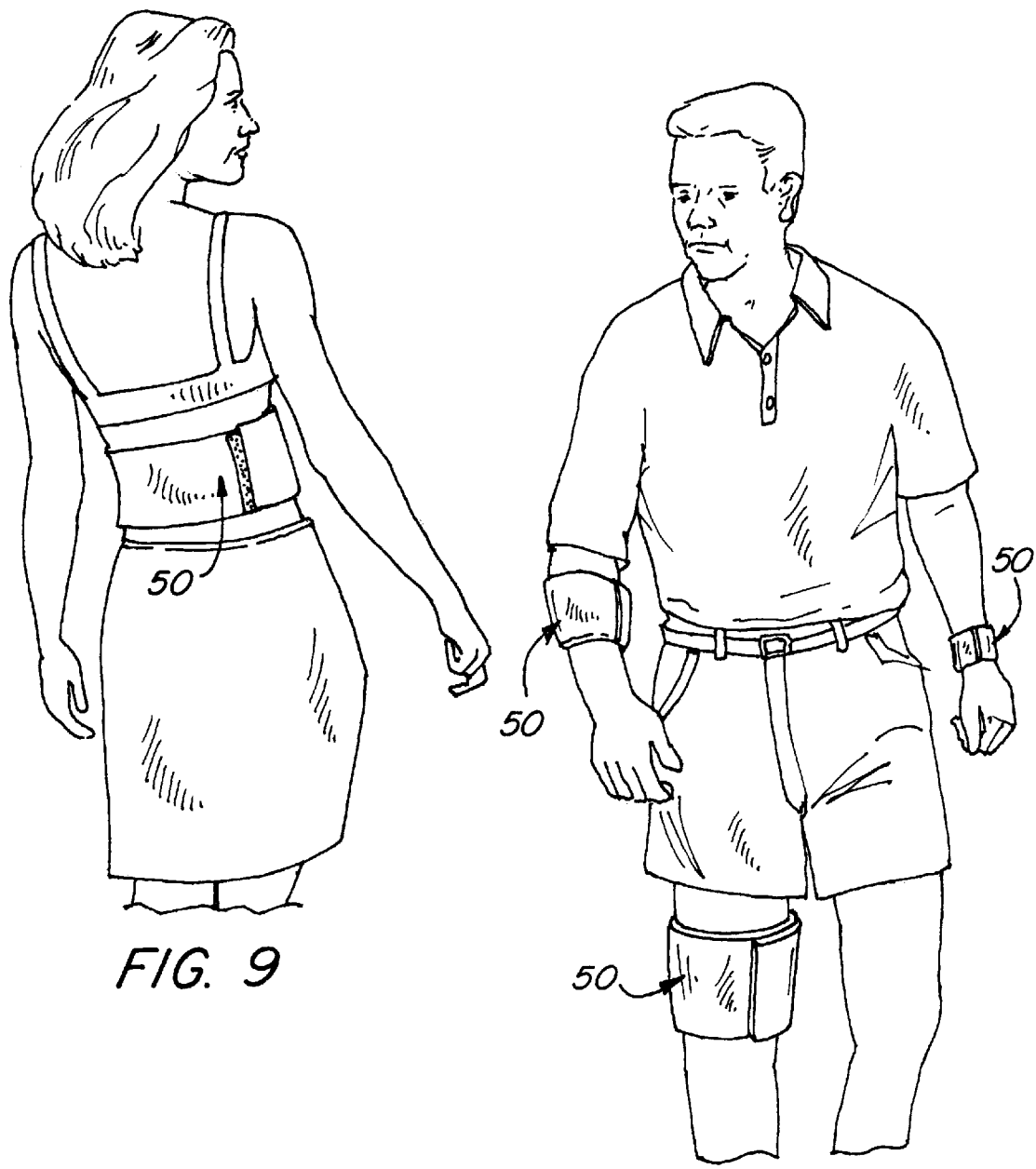
FIG. 9 is a view illustrating the modified bandage of FIGS. 6 to 8 as a waist wrap.
FIG. 10 is a view illustrating the modified bandage of FIGS. 6 to 8 sized for use as a leg wrap, arm wrap or wrist wrap.

As best seen in FIG. 7, a fastening means extends transversely at one end of the bandage 50. In the illustrated embodiment, a "Velcro" type fastener is shown. The "Velcro" fastener includes a strip or band of a hook-type material 55 connected to the facing sheet 51 at one end of the bandage or wrap 50. The covering sheet 52 includes a loop or pile strip 56 on the outer or rear surface adjacent the other end of the bandage as shown in FIG. 7. The arrangement is such that when the bandage or wrap 50 is wrapped about the injured part of the body, e.g. a leg, arm, waist, torso or the like, the bandage or wrap 50 can be maintained in the wrap position by overlapping the hook strip 55 over the other end of the bandage to engage the opposing loop or pile 56 connected to or forming part of the covering strip 52 so that the hook strip 55 attaches to the pile or loops 56 of the cover sheet 52 to secure the wrap or bandage 50 in position. It will be understood that the bandage 50 may be formed of variable lengths so as to be wrapped about the injured body part, as desired, and as shown in FIGS. 9 and 10.

It will be understood that the facing strip 51 is placed contiguous or in contact with the injured part so that the analgesic material, which is gradually being liberated or escaping from the facing sheet 51 in vapor form, is being applied directly to the injured body part. Simultaneously, the magnetic field generated by the magnets is also acting on the injured body part. It is believed that the magnet field generated by the magnets reduces pain caused by the injured body part by blocking the electrical impulses that carry the feeling of pain to the brain. It is also believed that the magnetic field, placed perpendicular to the blood vessels, causes a dilation of the blood vessel to enhance blood flow to the injured part, thereby increasing the flow of nutrient rich blood to the injured part to hasten healing. The analgesic or medicinal ingredient, on the other hand, functions to block the brain's ability to process the pain impulses and to feel the pain. Together, the magnetic field and the analgesic effect produced by the bandage, when in use, functions to both block the transmission and the receipt or processing of the pain concurrently; thereby hastening the healing of the injured part while minimizing and/or eliminating any feeling of pain during the healing process.

With pads 10 constructed as described with respect to FIGS. 1 to 5 wherein the facing sheet 16A comprises a resin or plastic material impregnated with a volatile analgesic material as herein described, or the bandage 50 formed as illustrated in FIGS. 6 to 8, the end result is virtually the same, i.e. the magnetic field generated by the magnets tends to block the electrical impulses that carry the feeling of pain to the brain and increase blood circulation to the injured part while the analgesic material being released from the impregnated material 16A or 51 onto the injured part tends to block the receipt of the pain by the brain to provide a synergistic effect which is greater than the use of either independently.

While the present invention has been described with respect to several preferred embodiments, it should be appreciated that various modifications may be made without departing from the spirit and scope of the present invention.

What is claimed is:

1. A magnetic therapy device comprising:
   a pad having a first surface and a second surface, said pad having a perimeter;
   a permanent magnet positioned within said pad;
   a first part of a fastener material extending along an edge of said pad on the first surface;

a second part of a fastener material extending along an edge of said pad on the second planar surface;

whereby a plurality of said pads can be fastened together to form a desired shape and placed against a portion of a body for magnetic therapy.

2. A magnetic therapy device as defined in claim 1 wherein one of said surfaces is formed of an organic solvent soluble synthetic resin material impregnated with a releasable analgesic ingredient whereby said analgesic material is gradually released from said one surface and imparted to the injured portion of a body.

3. A magnetic therapy device as defined in claim 2 wherein said synthetic resin material is selected from the group consisting of polyvinyl chloride, polyvinyl acetate, polyvinyl formal, polyvinyl acetal, polystyrene, and polyurethane.

4. A magnetic therapy device as defined in claim 3 wherein said analgesic ingredient is an essential oil.

5. A magnetic therapy device as defined in claim 3 wherein said one surface is impregnated with an aqueous emulsion of a surfactant and an analgesic material comprising an essential oil.

6. A magnetic therapy device as defined in claim 5 wherein said analgesic material is selected from the group consisting of oil of wintergreen, methyl salicylate, camphor, and eucalyptus.

7. A magnetic therapy device as in claim 2 wherein said pad has a quadrilateral shape.

8. A magnetic therapy device as in claim 2 wherein said quadrilateral shape is a rectangle.

9. A magnetic therapy device as in claim 2 wherein said first part of a fastener material is a hook fastener material.

10. A magnetic therapy device as in claim 2 wherein said second part of a fastener material is a loop fastener material.

11. A magnetic therapy device as in claim 2 wherein said first part of a fastener material extends around the entire perimeter of said pad.

12. A magnetic therapy device as in claim 2 wherein the second part of a fastener material covers the entire second surface.

13. A pad used in magnetic therapy comprising:

a planar foam substrate;

a loop fastener material placed over the entire surface of one side of said planar foam substrate;

a synthetic water insoluble resin material attached to said planar foam substrate forming a pocket;

an analgesic ingredient impregnated into said resin material whereby said analgesic ingredient is gradually released therefrom;

a plurality of permanent magnets placed within the pocket formed between said planar foam substrate and said mesh material;

a hook fastener material placed around the perimeter of said mesh material;

whereby a plurality of similarly constructed pads can be fastened together by attaching said loop fastener material on one pad to said mating hook fastener of another pad and placed against the body whereby the combined effect of the magnetic field generated by the magnets and the release of the analgesic ingredient enhances the therapeutic process.

14. A pad used in magnetic therapy as in claim 13 further comprising means for attaching said pad to a human body.

15. A method of applying a magnetic field and an analgesic effect to a human body comprising the steps of:

attaching a plurality of pads containing permanent magnets and an analgesic ingredient thereon whereby the analgesic ingredient is gradually released therefrom, together in a predetermined configuration;

placing the attached plurality of pads adjacent a desired portion of the human body; and holding the attached plurality of pads in place, whereby magnetic therapy and the combined release of the analgesic ingredient can be applied to any part of the injured human body to help enhance healing and reduce pain.

16. A magnetic therapy kit comprising:

a tray;

a plurality of pads placed within said tray, each of said plurality of pads having a permanent magnet placed therein and a facing strip formed of a water insoluble resin impregnated with an analgesic ingredient, a first fastener material placed around the perimeter on one surface, and a second mating fastener material placed on the other opposing surface;

a wrap placed within said tray, whereby said plurality of pads can be fastened together and placed adjacent any portion of the body.

17. A magnetic therapy kit as in claim 16, further comprising a book about magnetic therapy.

18. A magnetic therapeutic device comprising:

an elongated bandage adapted to be wrapped about an injured part to a body;

said bandage including a pair of superposed strips of material, means for circumscribingly securing said pair of superposed strips about the periphery thereof to define a pocket therebetween;

a plurality of permanent magnets disposed within said pocket in relative spaced relationship;

one of said superposed strips being formed of a synthetic water insoluble resin;

an analgesic ingredient impregnated in said resin strip so that the analgesic material is gradually released in a chemically unchanged dry state to the injured body part; and including a means for securing said bandage in the wrapped position, said last mentioned means including complementary hook and loop fasteners.

19. A magnetic therapeutic device as defined in claim 18 wherein said synthetic water insoluble resin forming said one superposed strip is selected from the group consisting of polyvinyl chloride, polyvinyl acetate, polyvinyl formal, polyvinyl acetal, polystyrene or polyurethane.

20. A magnetic therapeutic device as defined in claim 19, wherein said analgesic ingredient is selected from the group consisting of methyl salicylate, camphor, oil of wintergreen and eucalyptus.

21. A magnetic therapeutic device as defined in claim 18 wherein the other of said pair of strips is formed of a woven fabric.

22. A magnetic therapeutic device as defined in claim 21 and including a fastening means for securing said bandage in the wrapped position, said fastening means including a band of a "Velcro" material extending transversely of said bandage at one end thereof, and said other strip having an outer surface thereof formed with complementary mating means for engaging said "Velcro" band to maintain said bandage in the wrapped position about an injured body part.

23. A magnetic therapeutic device comprising:

an elongated bandage adapted to be wrapped about an injured body part;

said bandage including a facing strip formed of a synthetic water insoluble resin which is adapted to be placed in contact with an injured body part;

a superposed covering strip disposed contiguous to said facing strip;

means for attaching said facing strip to said covering strip about the peripheral edges thereof to define a pocket therebetween;

a plurality of permanent magnets disposed in spaced relationship within said pocket;

said facing strip being formed of a synthetic resin selected from the group consisting of polyvinyl chloride, polyvinyl formal, polyvinyl acetol, polyvinyl acetate, polystyrene, and polyurethane;

an analgesic ingredient impregnated into said facing strip;

said analgesic ingredient being selected from the group consisting of methyl salicylate, camphor, oil of wintergreen and eucalyptus;

means for securing said bandage in the wrapped position about the injured body part;

said securing means including a band of a "Velcro" type material extending transversely of said bandage at one end thereof to one of said strips;

and the other of said strips having a complementary "Velcro" type material so that in the wrapped position said band of "Velcro" material overlaps said complementary "Velcro" type material to secure the bandage in the wrapped position.

\* \* \* \* \*